United States Patent
Beger et al.

(10) Patent No.: US 9,078,704 B2
(45) Date of Patent: Jul. 14, 2015

(54) CONNECTING ELEMENT FOR A STABILIZATION SYSTEM FOR THE VERTEBRAL COLUMN, AND STABILIZATION SYSTEM FOR THE VERTEBRAL COLUMN

(75) Inventors: Jens Beger, Tuttlingen (DE); Beate Celmerowski, Gunningen (DE); Allan Maas, Constance (DE)

(73) Assignee: Aesculap AG, Tuttlingen (DE)

( * ) Notice: Subject to any disclaimer, the term of this patent is extended or adjusted under 35 U.S.C. 154(b) by 319 days.

(21) Appl. No.: 13/568,739

(22) Filed: Aug. 7, 2012

(65) Prior Publication Data

US 2013/0035725 A1   Feb. 7, 2013

Related U.S. Application Data

(63) Continuation of application No. PCT/EP2011/051838, filed on Feb. 8, 2011.

(30) Foreign Application Priority Data

Feb. 8, 2010 (DE) .......................... 10 2010 000 339

(51) Int. Cl.
*A61B 17/70* (2006.01)

(52) U.S. Cl.
CPC ......... *A61B 17/7026* (2013.01); *A61B 17/7004* (2013.01)

(58) Field of Classification Search
CPC ........... A61B 17/7026; A61B 17/7049; A61B 17/7002; A61B 17/7031; A61B 17/701; A61B 17/7004; A61B 17/7011; A61B 2017/00526; A61B 17/7032; Y10T 29/49613

USPC ......................................... 606/250–279, 86 A
See application file for complete search history.

(56) References Cited

U.S. PATENT DOCUMENTS 6,989,011 B2   1/2006   Paul et al.
7,329,258 B2   2/2008   Studer
(Continued)

FOREIGN PATENT DOCUMENTS

DE   100 04 712 C 1   8/2001
EP   1 523 949   6/2007
(Continued)

OTHER PUBLICATIONS

PCT Search Report for International Application No. PCT/EP2011/051838 Dated Aug. 14, 2012.
(Continued)

*Primary Examiner* — Pedro Philogene
(74) *Attorney, Agent, or Firm* — RatnerPrestia

(57) ABSTRACT

To improve a connecting element for a stabilization system for the vertebral column, which includes a first attachment section for fixing to a first bone fixation device, a second attachment section for fixing to a second bone fixation device, and an at least partially flexible intermediate section having at least one recess which is open at the sides, that at least one mechanical property of the intermediate section can be individually set in a simple and safe way, at least one movement limiting member is provided, which comprises a filling body and at least one stop device acting parallel or substantially parallel to the longitudinal axis and/or in the circumferential direction, and that the filling body, in a normal position in which no external forces act on the intermediate section, engage at least partially in the at least one recess.

23 Claims, 14 Drawing Sheets

(56) References Cited

U.S. PATENT DOCUMENTS

| | | |
|---|---|---|
| 7,335,200 B2 | 2/2008 | Carli |
| 7,377,921 B2 | 5/2008 | Studer et al. |
| 7,621,912 B2 | 11/2009 | Harms et al. |
| 8,012,180 B2 | 9/2011 | Studer et al. |
| 2005/0056979 A1 | 3/2005 | Studer et al. |
| 2005/0065514 A1 | 3/2005 | Studer |
| 2005/0085815 A1 | 4/2005 | Harms et al. |
| 2005/0131407 A1* | 6/2005 | Sicvol et al. .................... 606/61 |
| 2005/0154390 A1 | 7/2005 | Biedermann et al. |
| 2005/0267471 A1 | 12/2005 | Biedermann et al. |
| 2006/0184171 A1* | 8/2006 | Biedermann et al. ........... 606/61 |
| 2007/0088359 A1 | 4/2007 | Woods et al. |
| 2007/0191832 A1* | 8/2007 | Trieu ............................... 606/61 |
| 2007/0198088 A1 | 8/2007 | Biedermann et al. |
| 2007/0233085 A1 | 10/2007 | Biedermann et al. |
| 2008/0033435 A1 | 2/2008 | Studer et al. |
| 2008/0221681 A1 | 9/2008 | Trieu et al. |
| 2008/0234736 A1* | 9/2008 | Trieu et al. .................... 606/250 |
| 2009/0326584 A1 | 12/2009 | Slivka et al. |
| 2010/0042156 A1 | 2/2010 | Harms et al. |

FOREIGN PATENT DOCUMENTS

| | | |
|---|---|---|
| EP | 1 450 708 | 11/2007 |
| WO | WO 2006/101737 | 9/2006 |
| WO | WO 2007/090015 | 8/2007 |
| WO | WO 2008/003047 | 1/2008 |
| WO | WO 2008/033976 | 3/2008 |
| WO | WO 2008/073830 | 6/2008 |
| WO | WO 2011/038141 | 3/2011 |

OTHER PUBLICATIONS

PCT Search Report for International Application No. PCT/EP2011/051838 Dated Apr. 28, 2011.

* cited by examiner

CONNECTING ELEMENT FOR A STABILIZATION SYSTEM FOR THE VERTEBRAL COLUMN, AND STABILIZATION SYSTEM FOR THE VERTEBRAL COLUMN

CROSS-REFERENCE TO RELATED APPLICATIONS

This application is a continuation of international application number PCT/EP2011/051838, filed on Feb. 8, 2011, and further claims the benefit of priority of German application number 10 2010 000 339.5, filed on Feb. 8, 2010, the contents of both documents being incorporated herein by reference in their entireties and for all purposes.

FIELD

The present invention relates to connecting elements for a stabilization systems for the vertebral column generally, and more specifically to a connecting element for a stabilization system for the vertebral column, comprising a first attachment section for fixing to a first bone fixation device, a second attachment section for fixing to a second bone fixation device, and an at least partially flexible intermediate section arranged or formed between the first and second attachment sections, the intermediate section having at least one recess which is open at the sides in a direction transverse to a longitudinal axis defined by the intermediate section.

The present invention also relates to stabilization systems for the vertebral column generally, and more specifically to a stabilization system for the vertebral column, comprising at least one first bone fixation device, at least one second bone fixation device, and a connecting element, the connecting element comprising a first attachment section for fixing to the at least one first bone fixation device, a second attachment section for fixing to the at least one second bone fixation device, and an at least partially flexible intermediate section arranged or formed between the first and second attachment sections, the intermediate section having at least one recess which is open at the sides transversely to a longitudinal axis defined by the intermediate section.

BACKGROUND

Both a connecting element and a stabilization system for the vertebral column of the kind described at the outset are known, for example, from US 2006/0184171 A1. The connecting element disclosed therein comprises an intermediate section in the form of a loop-shaped rod, with the loops running along a connection axis from a first to a second end of the connecting element, alternatingly on two opposite sides of the connection axis.

A stiffness of the intermediate section and, therefore, of the connecting element in its entirety is defined by the configuration of the intermediate section. Therefore, in particular, after an implantation, a change in the stiffness or other mechanical properties of the intermediate section is no longer possible. If changes are desired, the connecting element must be completely exchanged. Depending on a patient's physiology, the known systems require a large number of connecting elements with different stiffnesses and possibly dimensions to be kept ready so as to enable an operating surgeon to choose in the light of his findings the best suited connecting element for the patient.

Therefore, it would be desirable to provide a connecting element and a stabilization system for the vertebral column so that at least one mechanical property of the connecting element, in particular, of the intermediate section thereof, can be individually set in a simple and safe way.

SUMMARY

In a first aspect of the invention, a connecting element for a stabilization system for the vertebral column comprises a first attachment section for fixing to a first bone fixation device, a second attachment section for fixing to a second bone fixation device, and an at least partially flexible intermediate section arranged or formed between the first and second attachment sections. Said intermediate section has at least one recess which is open at the sides in a direction transverse to a longitudinal axis defined by the intermediate section. At least one movement limiting member is provided, which comprises a filling body and at least one stop device acting at least in one of a direction parallel or substantially parallel to the longitudinal axis and a circumferential direction. And the filling body, in a normal position in which no external forces act on the intermediate section, engages at least partially in the at least one recess.

In a second aspect of the invention, a connecting element for a stabilization system for the vertebral column comprises a first attachment section for fixing to a first bone fixation device, a second attachment section for fixing to a second bone fixation device, and an at least partially flexible intermediate section arranged or formed between the first and second attachment sections. Said intermediate section has at least one recess which is open at the sides in a direction transverse to a longitudinal axis defined by the intermediate section. Said connecting element has an outside surface which is machined at least partially by a blasting process.

In a third aspect of the invention, a stabilization system for the vertebral column comprises at least one first bone fixation device, at least one second bone fixation device, and a connecting element. Said connecting element comprises a first attachment section for fixing to the at least one first bone fixation device, a second attachment section for fixing to the at least one second bone fixation device, and an at least partially flexible intermediate section arranged or formed between the first and second attachment sections. Said intermediate section has at least one recess which is open at the sides transversely to a longitudinal axis defined by the intermediate section. At least one movement limiting member is provided, which comprises a filling body and at least one stop device acting at least in one of a direction parallel or substantially parallel to the longitudinal axis and a circumferential direction. And the filling body, in a normal position in which no external forces act on the intermediate section, engages at least partially in the at least one recess

BRIEF DESCRIPTION OF THE DRAWINGS

The foregoing summary and the following description may be better understood in conjunction with the drawing figures, of which.

DETAILED DESCRIPTION

Figure 1:
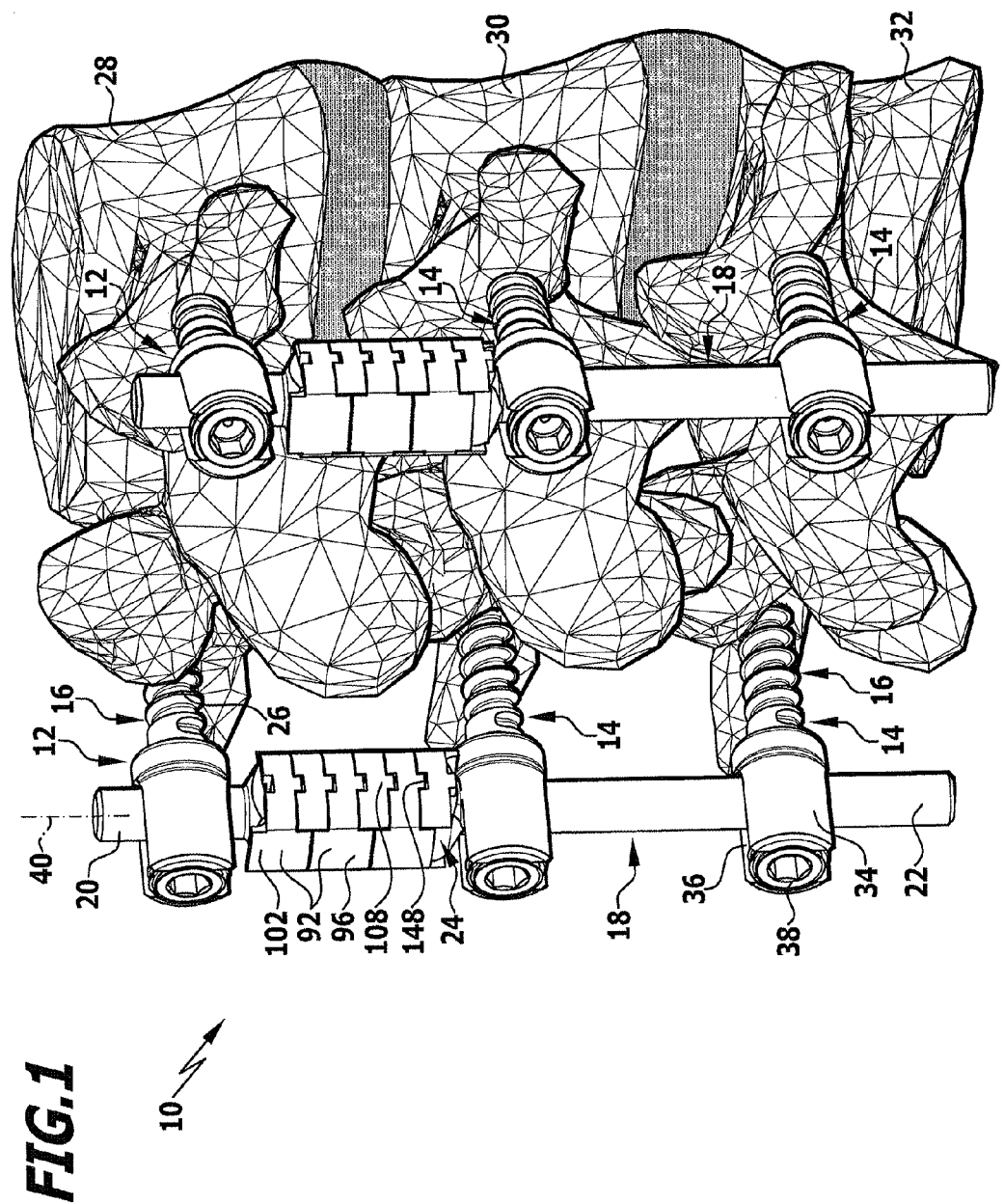
FIG. 1 shows a diagrammatic overall view of a stabilization system for the vertebral column, which is fixed to a vertebral column.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a connecting element for a stabilization system for the vertebral column, comprising: a first attachment section for fixing to a first bone fixation device, a second attachment section for fixing to a second bone fixation device, and an at least partially flexible intermediate section arranged or formed between the first and second attachment sections, said intermediate section having at least one recess which is open at the sides in a direction transverse to a longitudinal axis defined by the intermediate section, wherein at least one movement limiting member is provided, which comprises a filling body and at least one stop device acting at least in one of a direction parallel or substantially parallel to the longitudinal axis and a circumferential direction, and wherein the filling body, in a normal position in which no external forces act on the intermediate section, engages at least partially in the at least one recess.

The at least one movement limiting member, which is in engagement with the intermediate section in the described manner, enables movability of the intermediate section to be limited in a defined manner. In particular, depending on the configuration of the movement limiting member and depending on the number of recesses and movement limiting members, a compression, a flexion and a rotation or twisting of the intermediate section can be selectively allowed, limited or completely excluded. In other words, this means that in dependence upon the configuration of the movement limiting member, in particular, of the stop device, mechanical properties of the connecting element, in particular, of the intermediate section can be specifically set. It is thus possible for an operating surgeon, to already select a standard connecting element with an at least partially flexible intermediate section during a surgical operation and to adapt the mechanical properties to the specific requirements by fitting one or more movement limiting members. In particular, it is favorable if the filling body, in the normal position, engages with clearance or with play in the recess. In this way, in particular, a specific flexion or compression of the intermediate section can be enabled or limited by the filling body of the movement limiting member.

It is advantageous if the stop device comprises at least one stop arranged on, formed on and/or protruding from the filling body and acting parallel or substantially parallel to the longitudinal axis and/or in the circumferential direction. Movability of the intermediate section can be easily and safely limited or eliminated by providing at least one stop on the filling body in the described manner. In particular, this configuration is favorable if two, three or more movement limiting members are provided, each engaging in a recess of the intermediate section. The at least one stop may, in particular, have stop surfaces which face in the direction or substantially in the direction of the longitudinal axis or in the circumferential direction.

The connecting element can be manufactured particularly easily if a plurality of recesses are provided, which are open alternatingly facing in opposite directions. Such a configuration can be easily achieved by, for example, serpentine or zigzag deformation of a rod or strip-shaped material. It is also conceivable to manufacture it by machining with chip removal from a solid material. Owing to the formation of neighboring recesses turned, so to speak, through 180° in relation to the longitudinal axis, a flexion of the intermediate section in opposite directions, if required, also in a specifically different way, can be influenced by appropriately designed movement limiting members.

It is favorable if a movement limiting member is allocated to each recess so as to enable as continuous an influence as possible on the intermediate section and its mechanical properties. In principle, it is also possible to design and provide movement limiting members comprising two filling bodies so as to connect or couple neighboring or next but one recesses to each other. For example, a movement limiting member may also completely or partially fill out all recesses open so as to face in the same direction by a corresponding number of filling bodies.

The connecting element is particularly simple to manufacture and assemble if all movement limiting members are of identical construction. In this way, confusion cannot occur when assembling the connecting element.

In accordance with a further preferred embodiment of the invention, it may be provided that movement limiting members turned relative to one another through 180° about the longitudinal axis are inserted into neighboring recesses. In particular, this may be the case with movement limiting members of identical construction. This is also advantageous if exactly one movement limiting member is allocated to each recess and if neighboring recesses are open so as to face in opposite directions.

It is advantageous if stop devices of neighboring movement limiting members, in the normal position, lie at least partially in a non-contacting manner opposite each other and, in a position deflected from the normal position, lie against each other. For example, the stop devices lying opposite each other in the normal position can be separated from each other or spaced from each other by a gap. A maximum possible deformation of the intermediate section, for example, a compression or a flexion can thus be specifically set by a width of the gap. A deformation is limited by the stop devices lying against each other in the position deflected from the normal position and by further movement thereof, for example, towards each other, no longer being possible.

Stop devices can be easily formed in the described manner if the stops acting parallel or substantially parallel to the longitudinal axis are spaced from each other in the normal position and abut against each other in the deflected position. This configuration can be achieved with both stops acting in the longitudinal direction and stops acting in the circumferential direction in order to specifically allow, in particular, compression movements and rotational movements, for example, twistings, of the intermediate section within a certain range and to limit these beyond that.

Preferably, the stops acting in the circumferential direction, engage one another with positive locking or substantially with positive locking in the normal position and/or in the deflected position. Owing to positive connections formed in this manner, in particular, a rotational or twisting movement of neighboring recesses of the intermediate section can be completely or substantially completely prevented by interacting movement limiting members. For example, a rotation-locking or twist-preventing device can thus be formed in a simple way.

The stop device can be formed in a particularly simple way if each movement limiting member comprises a stop device with two stops facing in opposite directions. In particular, the stops may be formed by side faces or stop surfaces, defining surface areas, on the filling body or on projections protruding from the filling body or on recesses formed on the filling body.

The design of the connecting element and, therefore, its construction and manufacture are particularly simple if the at least one movement limiting member and/or the intermediate section are formed mirror-symmetrically in relation to a mirror plane containing the longitudinal axis.

It is also advantageous if the connecting element comprises an anti-twisting device for preventing twisting of the intermediate section about the longitudinal axis. The anti-twisting device enables, in particular, shear forces acting transversely to the longitudinal axis and/or in the circumferential direction to be absorbed and the connecting element to be stabilized.

It is particularly favorable if the anti-twisting device comprises the at least one stop acting in the circumferential direction. The anti-twisting device may, of course, also comprise two or more stops acting in the circumferential direction, which, in turn, may be defined or formed by stop surfaces. Such stops preferably directly counteract shear or twisting forces.

In accordance with a further preferred embodiment of the invention, it may be provided that the anti-twisting device comprises at least one coupling device for coupling neighboring movement limiting members whose filling bodies engage in neighboring recesses of the intermediate section. In this way, areas or sections of the intermediate section limited by the recesses can be directly or indirectly coupled to one another via the anti-twisting device and a twisting of the intermediate section limited or even prevented.

The at least one coupling device can be formed particularly easily if it comprises first and second coupling members which engage with force locking and/or positive locking, and if a first coupling member of a movement limiting member faces in the direction of the second coupling member of a movement limiting member which is at least partially in engagement with a neighboring recess. In particular, neighboring movement limiting members or next but one neighbors or possibly even more remote neighbors can be coupled to one another in a simple way by the thus formed coupling members.

It is advantageous if the at least one movement limiting member comprises at least one first coupling member and at least one second coupling member, which are each allocated to a coupling device, and if the at least one first coupling member and the at least one second coupling member are formed or arranged so as to face in the opposite directions. The first and second coupling members of a movement limiting member thus each form a part of a coupling device. In other words, in this case, each movement limiting member is at least partly associated with two coupling devices for coupling the movement limiting member to two further movement limiting members.

The design of the connecting element is particularly simple if the first and second coupling members comprise or form the stops acting in the circumferential direction. In particular, these may comprise stop surfaces facing in the circumferential direction or at least in a direction transverse to the longitudinal axis.

In particular, neighboring movement limiting members can be coupled to one another in a simple way if the at least one first coupling member and the at least one second coupling member are aligned parallel to the longitudinal axis. In particular, the coupling members may be in the in the form of projections and/or recesses, which, in a coupling position, may engage with one another with force locking and/or positive locking.

It is favorable if the at least one recess, in the normal position, comprises an insertion opening facing transversely to and away from the longitudinal axis for inserting the filling body in a direction transverse to and towards the longitudinal axis. Assembly of the connecting element then becomes particularly simple as the filling bodies of the movement limiting members can then be easily inserted from the side in the direction towards the longitudinal axis into the recesses.

The insertion opening preferably forms a constriction. Owing to corresponding configuration of the filling body which, for example, may have a narrowing or cross-sectional taper corresponding to the constriction, the movement limiting member can be undetachably secured to the intermediate section by engagement of the filling body and the recess without any further auxiliary means.

The movement limiting member can be held on the intermediate section in a simple and safe way if the recess widens on the inside starting from the constriction. For example, a filling body can even be held in the recess if it does not fill it out completely, i.e., for example, if it has clearance, but has a maximum cross section or a cross-sectional area which is larger than a cross-sectional area defined by the insertion opening. The described variants apply, in particular, to the normal position if there are no external forces acting on the connecting element, in particular, on its intermediate section. For example, to insert the filling bodies into the recesses, it may also be favorable if the intermediate section undergoes such deformation that the respective insertion opening widens for insertion of the filling body of the movement limiting member.

To form as compact a connecting element as possible and to protect the recess, it is advantageous if the movement limiting member comprises a closing element for closing the insertion opening.

The movement limiting member can be manufactured particularly easily if the closing element is arranged or formed on the filling body.

In particular, the stability of the movement limiting member can be increased by the at least one stop device comprising the closing element. For example, outer side surfaces or edges of the closing element may form stops or stop surfaces of the stop device. The closing element can thus assume at least a double function.

In accordance with a further preferred embodiment of the invention, it may be provided that closing elements of next but one movement limiting members, in the normal position, lie against each other or are spaced from each other by a gap. In particular, with neighboring recesses open alternatingly in opposite directions, next but one recesses can thus be coupled to each other by movement limiting members in engagement with these recesses in order, for example, to limit a compression movement or a flexion movement.

The manufacture of the intermediate section is particularly simple if the at least one recess is open at the sides so as to face in two directions opposite to each other, and if the at least one movement limiting member at least partially closes the at least one recess at least at one side. In particular, if the intermediate section is made by machining with chip removal from a solid material, the movement limiting member at least partially closing the recess can prevent the filling body from becoming unintentionally detached from the recess.

In order to position the at least one movement limiting member in a defined manner in a recess, it is favorable if it completely or substantially completely closes the at least one recess on both sides. In this way, in particular, a movement can be prevented in a direction both transverse to the longitudinal axis and transverse to a direction of insertion, defined by the insertion opening, of the at least one movement limiting member relative to the recess.

The recess open at the sides can be closed at the sides in a simple way if the at least one movement limiting member comprises at least one side closure element for at least partially closing the at least one recess at the sides.

The at least one movement limiting member can be arranged in a particularly safe and defined manner at at least one recess if it comprises two side closure elements for closing the at least one recess at two opposite sides. As explained above, a movement of the filling body transverse to the longitudinal axis and transverse to the direction of insertion can be prevented by the two closure elements.

The at least one movement limiting member can be manufactured in a simple way if the at least one side closure element is formed so as to protrude from the side of the filling body. In particular, it may be formed so as to project in directions parallel to the longitudinal axis beyond the filling body.

It is advantageous if the at least one side closure element comprises or carries at least one of the stops acting parallel or substantially parallel to the longitudinal axis or in the circumferential direction. The movement limiting member and, therefore, the connecting element in its entirety can thus be constructed in a particularly compact manner. The side closure element can, therefore, simultaneously assume a number of functions.

The filling body preferably has at least one cross-sectional taper. In particular, with a narrowed insertion opening, it is thus possible, without further auxiliary means, for the at least one movement limiting member, at least in the normal position, to be brought into engagement with the intermediate section without it being able to become unintentionally detached from it.

To prevent rejecting reactions, it is favorable if the at least one movement limiting member is made from a biocompatible material.

The at least one movement limiting member can be manufactured in a particularly cost-effective manner if the biocompatible material is a plastic. The plastic preferably is or contains polyethylene, polyether ether ketone, polyurethane, polycarbonate urethane or at least one fiber-reinforcing plastic.

The manufacture of the at least one movement limiting member can be further simplified if it is of one-piece configuration. For example, it can thus be manufactured by injection molding.

The at least one movement limiting member can be manufactured in a simple and cost-effective manner if it is in the form of an injection molded part. For example, it may be a plastic injection molded part.

In accordance with a further preferred embodiment of the invention, it may be provided that a plurality of movement limiting members in engagement with the intermediate section are provided, which define a common and substantially cylindrical enveloping contour. In this way, injury to surrounding body tissue can be substantially prevented. In particular, owing to the described closing and closure elements, it is practically impossible for body tissue surrounding the connecting element to penetrate into the recesses of the intermediate section and get trapped in these. Owing to the cylindrical enveloping contour, in particular, a substantially rod-shaped design of the connecting element can be achieved.

To enable a basic flexibility of the intermediate section, it is favorable if it comprises at least three recesses. It may, of course, also comprise four, five or more recesses. Typically, a flexibility of the intermediate section can be increased by increasing the number of recesses.

The intermediate section is preferably of elastic construction. Firstly, it is, in this way, possible to reduce a risk of breakage of the connecting element. Secondly, the elasticity of the intermediate section can be used to independently, i.e., automatically, return the connecting element to the normal position again after deflection.

It is advantageous if the connecting element comprises a resetting device for automatically returning the connecting element from a deflected position in which it is deflected from the normal position back into the normal position. Forces required for deforming the connecting element, in particular, the intermediate section, can be predefined by the resetting device. Owing to the resetting device, the further the connecting element is to be deflected from the normal position, the higher are the forces that are required.

The connecting element can be manufactured particularly easily if the resetting device comprises at least one resetting element for automatically returning the connecting element from the deflected position to the normal position.

It is favorable if the resetting element is in the form of a spring element. In particular, the resetting element may be in the form of a leaf spring. Also conceivable are a plurality of resetting elements which couple individual sections of the intermediate section to one another. In particular, if the last-mentioned sections of the intermediate section are rigid and inflexible, a flexibility of the intermediate section can thus be predefined in a defined manner by the provision of the resetting elements.

A particularly compact connecting element can be formed if the intermediate section forms or comprises the resetting element. For example, the intermediate section may be in the form of a leaf spring wound in a serpentine manner, which thus defines in cross section substantially drop-shaped recesses, with neighboring recesses being open so as to face in opposite directions and away from the longitudinal axis.

It is advantageous if the intermediate section is wound in a serpentine or zigzag manner from a strip-shaped or rod-shaped material. For example, the intermediate section may thus be easily manufactured from a leaf spring. Alternatively, it may, however, also be manufactured from a solid material, for example, by milling or erosion. In particular, manufacture from a solid material makes it possible to form the connecting element entirely in one piece. If the attachment sections and the intermediate section are manufactured separately from one another, the parts may, in particular, be connected to one another by welding.

It is favorable if the intermediate section comprises a plurality of curved sections, which extend alternatingly away from opposite sides of the longitudinal axis. In particular, this makes it possible to form the intermediate section in a serpentine or zigzag manner. Furthermore, the curved sections may define both a flexibility and, depending on the choice of material, also a desired elasticity of the intermediate section.

To reduce the risk of injury to surrounding tissue, it is favorable if the curved sections are convexly curved facing away from the longitudinal axis. It is thus possible to manufacture them substantially free of sharp edges.

It is also advantageous if the curved sections are connected to one another by straight-lined or plane sections. In particular, they serve as spacers between the curved sections and do not necessarily have to be flexible or elastic. Alternatively, the curved sections may, however, also be inflexible or inelastic, the straight-lined or plane sections, on the other hand, flexible or elastic.

To increase the stability of the intermediate section, it is favorable if the straight-lined or plane sections intersect a longitudinal axis defined by the intermediate section. In particular, a spacing between consecutive curved sections can thus be set in a defined manner. In particular, a movability or flexibility of the intermediate section, in particular, for a flexion and/or extension movement of the attachment sections of the connecting element relative to one another can be defined by the spacings between the consecutive curved sections.

To reduce the maximum bending stresses in a curved or arcuate section of the intermediate section, it is favorable if a thickness of the intermediate section in the area of the curved sections is greater than in the area of the plane sections.

It is favorable if the thickness of the curved sections is about 1.1 times to about 1.5 times a thickness of the plane sections. The thickness of the curved sections is preferably about 1.3 times to about 1.35 times the thickness of the plane sections. The specified ranges are exceptionally well suited for minimizing maximally occurring bending stresses in the area of the curved sections. All in all, a stability of the intermediate section and, therefore, also of the entire connecting element can thus be increased.

It is advantageous if a stiffness of the intermediate section has a value ranging from 30 N/mm to about 150 N/mm. The specified stiffness of the intermediate section may, in particular, relate to its basic shape without coupled movement limiting members. The stiffness of the intermediate section can be increased, in particular, beyond the specified value of about 150 N/mm by suitable movement limiting members.

Particularly good flexible or elastic properties of the intermediate section can be achieved if it is formed from a flat or substantially flat material. For example, it can be formed from a substantially flat material in which sections of different thickness alternate, with the intermediate section then preferably being formed such that the thicker sections form curved sections of the intermediate section, and the thinner sections of the substantially flat material form plane or flat sections connecting the curved sections.

It is favorable if the intermediate section comprises two side faces facing away from each other, which, in the normal position, extend parallel or substantially parallel to each other. The side faces may, in turn, in the case of a section wound in a serpentine manner, also be formed so as to extend in a serpentine manner. The side faces may, in particular, serve as stops for closure elements of the movement limiting members.

Manufacture of the connecting element is particularly simple if the side faces extend, in the normal position, parallel or substantially parallel to a center plane containing the longitudinal axis.

To increase the compatibility of the connecting element with stabilization systems for the vertebral column that are available on the market, it is advantageous if the first attachment section and/or the second attachment section is/are rod-shaped.

The first attachment section and/or the second attachment section preferably have a circular or substantially circular cross section. The connecting element may thus, in particular, instead of a round rod-shaped connecting element, be combined with known stabilization systems for the vertebral column. Of course, oval or N-angular cross sections, in particular, triangular, quadrangular or hexagonal cross sections are also possible, which are adapted to corresponding receptacles on bone fixation devices.

To avoid rejecting reactions, it is favorable if the intermediate section and/or the first attachment section and/or the second attachment section is/are made from a biocompatible material.

The biocompatible material preferably is or contains a titanium alloy, a cobalt chrome alloy, polyether ether ketone or carbon fiber-reinforced polyether ether ketone. In particular, the aforementioned materials are biocompatible and exceptionally well suited as implant materials.

It is advantageous if the connecting element has an outside surface which is machined at least partially by a blasting process. Such a design is, in particular, also advantageous for a connecting element for a stabilization system for the vertebral column, comprising a first attachment section for fixing to a first bone fixation device, a second attachment section for fixing to a second bone fixation device, and an at least partially flexible intermediate section arranged or formed between the first and second attachment sections, the intermediate section having at least one recess which is open at the sides in a direction transverse to a longitudinal axis defined by the intermediate section. Machining the outside surface by a blasting process allows, in particular, an endurance strength of the connecting element to be significantly increased, which is highly advantageous, in particular, in permanently installed implants.

The at least partially machined surface is preferably machined by a shot peening process. Such a process is particularly easy to perform. Where appropriate, it is also possible to specifically machine only individual areas of the outside surface. In particular, steel or glass balls may be used as balls for shot peening the connecting element.

It may also be favorable if the at least partially machined surface is machined by a "laser peening" process, in which the surface is subjected to shock waves generated by pulsed laser beam action in order to produce residual compressive stresses. As also in the shot peening process, residual compressive stresses can be introduced by impacting with a laser. These counteract, in particular, fatigue cracks.

The manufacturing expenditure for the connecting element may, in particular, be reduced by the entire outside surface being completely machined. In this way, there is no need to cover individual areas of the surface of the connecting element before and during the blasting.

It is advantageous if the outside surface is machined except for the side faces of the intermediate section. The side faces of the intermediate section are, in particular, side faces extending parallel or substantially parallel to a center plane containing the longitudinal axis. The side faces are preferably covered before the blasting treatment. In this way, it is possible to prevent, in particular, a thin-walled intermediate section formed from a flat material from becoming plastically deformed in the area of the side faces. Such side deformations are more likely to adversely affect an endurance strength of the intermediate section. Depending on the size and thickness of the intermediate section and the side faces, the blasting processes used may cause impact craters or bombardment craters to occur in an order of magnitude of a wall thickness of the intermediate section. Therefore, deformations of the side faces in the form of corners or notches may be formed, which are then more likely to reduce an endurance strength of the intermediate section.

In accordance with a further preferred embodiment of the invention, it may be provided that the outside surface comprises outer surfaces of the first attachment section, the second attachment section and the intermediate section, and that the outer surfaces of the first attachment section and/or of the second attachment section and/or of the intermediate section are machined. It is, therefore, in particular, possible to selectively treat surfaces of one or both attachment sections and/or of the intermediate section with a blasting process. Alternatively to the shot peening process, a thickness of the residual compressive stress layer can be further increased, more specifically, by about one millimeter, by the so-called "laser peening" process.

The invention further relates to a stabilization system for the vertebral column, comprising: at least one first bone fixation device, at least one second bone fixation device, and a connecting element, said connecting element comprising a first attachment section for fixing to the at least one first bone fixation device, a second attachment section for fixing to the at least one second bone fixation device, and an at least partially flexible intermediate section arranged or formed between the first and second attachment sections, said intermediate section having at least one recess which is open at the sides transversely to a longitudinal axis defined by the intermediate section, wherein at least one movement limiting member is provided, which comprises a filling body and at least one stop device acting at least in one of a direction parallel or substantially parallel to the longitudinal axis and a circumferential direction, and wherein the filling body, in a normal position in which no external forces act on the intermediate section, engages at least partially in the at least one recess.

It is favorable if the stabilization system for the vertebral column in accordance with the invention comprises at least one of the connecting elements described above. It then also has the advantages described above in conjunction with the preferred embodiments of the connecting elements.

A connecting elements can be fixed to a bone in a simple and safe way if the at least one first bone fixation device and/or the at least one second bone fixation device are in the form of a bone screw.

To enable the stabilization system for the vertebral column to be adapted as optimally as possible to individual patient physiologies, it is favorable if the bone fixation device comprises a bone anchoring section and a retaining section articulatedly mounted thereon, in an adjustment position, the retaining section having an attachment section receptacle for one of the attachment sections of the connecting element. This design makes it possible to align the retaining section in a desired manner, more specifically, substantially independently of an orientation of the bone anchoring section. The retaining section is preferably held on the bone anchoring section so as to be polyaxially pivotable in the adjustment position and immovably fixable in an implantation position. It may also be favorable if at least one of the two attachment sections of the connecting element has a length which makes it possible for it to be fixed to two bone fixation devices. If the latter are fixed to neighboring vertebrae, a first attachment section of the connecting element can therefore be used to rigidly connect two neighboring vertebrae to each other, i.e., to stiffen a section of the vertebral column. By means of the specially designed intermediate section, one of the two vertebrae can be at least partially movably coupled to a further vertebra to which is fixed a further bone fixation device to which the second attachment section can be fixed, in order to leave a residual mobility in a defined manner.

DETAILED DESCRIPTION

A stabilization system for the vertebral column, generally designated by reference numeral 10, is shown diagrammatically in FIG. 1. It comprises first bone fixation devices 12 and second bone fixation devices 14, which in the embodiment shown diagrammatically in FIG. 1 are all in the form of identical bone screws 16, but may also be of different design. The stabilization system 10 for the vertebral column further comprises substantially rod-shaped connecting elements 18, which comprise a first attachment section 20 for attachment to a bone screw 16, a second attachment section 22 for attachment to two bone screws 16, and an at least partially flexible intermediate section 24 arranged or formed between the first and second attachment sections 20, 22.

The bone screws 16 each comprise a bone anchoring section 26 with a bone thread for anchoring in a bone, for example, in one of the vertebrae 28, 30 and 32, shown diagrammatically in FIG. 1, of a vertebral column. Furthermore, each bone screw 16 comprises a retaining section 34 in the form of a fork head which, in an adjustment position, is mounted in an articulated manner on the bone anchoring section 26. The fork head comprises an attachment section receptacle 36 for one of the attachment sections 20, 22 of a connecting element 18. An attachment section 20, 22 introduced into the attachment section receptacle 36 can be fixed in a clamped manner in an implantation position by a clamping screw 38. By fixing the attachment section 20, 22 to the retaining section 34, a relative position between the bone anchoring section 26 and the retaining section 34 is preferably also fixed in a permanent manner.

The attachment sections 20, 22 are each round bar-shaped and, therefore, have a circular cross section. They are formed in one piece with the intermediate section 24. Preferably, as in the embodiment of a connecting element 18 shown in the Figures, the attachment sections 20 and 22 define a common longitudinal axis 40, which also defines a longitudinal axis of the intermediate section 24.

The intermediate section 24 is formed at a first end of the attachment section 20 and forms in the area of transition 42 to the attachment section 20 a substantially flat, cuboidal end plate 44. Adjoining a longitudinal side thereof, transversely away from the longitudinal axis 40, is a curved section 46. This extends over an angular range of somewhat more than 180°. Adjoining the curved section 46 is a flat plane section 48, which, in turn, continues into a curved section 50 which, also facing away from the longitudinal axis 40, is convexly curved. The curved sections 46 and 50 do, however, face in opposite directions. An end face 52 of the end plate 44 facing in the direction of the second attachment section 22 is somewhat inclined to the plane section 48. Adjoining the curved section 50 is, in turn, a plane section 54 which extends parallel to the end face 52. The serpentine contour of the intermediate section 24 continues with a further plane section 48, an adjoining curved section 50, an adjoining plane section 54, an adjoining curved section 46, an adjoining plane section 48 and a last, adjoining curved section 50, which continues into an end plate 56 shaped in accordance with the end plate 44 and having an end face 58 which faces in the direction of the first attachment section 20 and extends parallel to the plane sections 54 and, consequently, also to the end face 52.

Depending on the choice of material from which the connecting element 18 is made, a stiffness of the intermediate section 24 ranges from approximately 30 N/mm to approximately 150 N/mm. The intermediate section 24 in its entirety is formed from a substantially flat material or from a solid material by machining with chip removal, for example, milling or eroding. Transversely away from the longitudinal axis 40, the intermediate section 24 comprises two side faces 60 and 62 which, in a normal position in which no external forces act on the intermediate section 24, extend parallel to each other and face away from each other. These also extend parallel to a plane of symmetry 64 of the connecting element 18 containing the longitudinal axis 40.

Owing to the serpentine design of the intermediate section 24, a total of six recesses 66, 68 are formed in the embodiment shown in the Figures. The recesses 66 face in the same direction as that in which the convexly curved sections 50 are open and face, but the recesses 68 face in the opposite direction, i.e., in the direction in which the convexly curved sections 46 face. Each of the recesses 66, 68 defines an insertion opening 70 and 72, respectively, lying opposite a curved section 46 and 50, respectively, and facing in the respective opposite direction. Each recess 66, 68 is delimited by two plane sections 48 and 54 extending towards each other in the direction of the respective insertion opening 70, 72 so that a cross section of the respective, approximately drop-shaped recess 66, 68 increases from the insertion opening 70 and 72, respectively, in the direction towards the curved sections 46, 50 further delimiting the recesses 66, 68. Each insertion opening 70, 72 therefore defines a constriction 74. The recesses 66, 68 are, therefore, each open at the sides in a direction transverse to the longitudinal axis 40.

A thickness 76 of the intermediate section 24 in the area of the curved sections 46, 50 is greater than in the area of the plane sections 48, 54. The thickness 76 is from about 1.1 times to about 1.5 times the thickness 78, preferably from about 1.3 times to about 1.35 times. In the embodiment shown in the Figures, the thickness 76 is about 0.8 mm, the thickness 78 about 0.6 mm. An inner radius of the curved sections 46, 50 is about 1.6 mm, an outer radius about 2.2 mm.

To increase the endurance strength of the connecting element 18, its outside surface 80 may be at least partially machined by a blasting process. This is represented diagrammatically in FIGS. 10 to 14.

Figure 10:
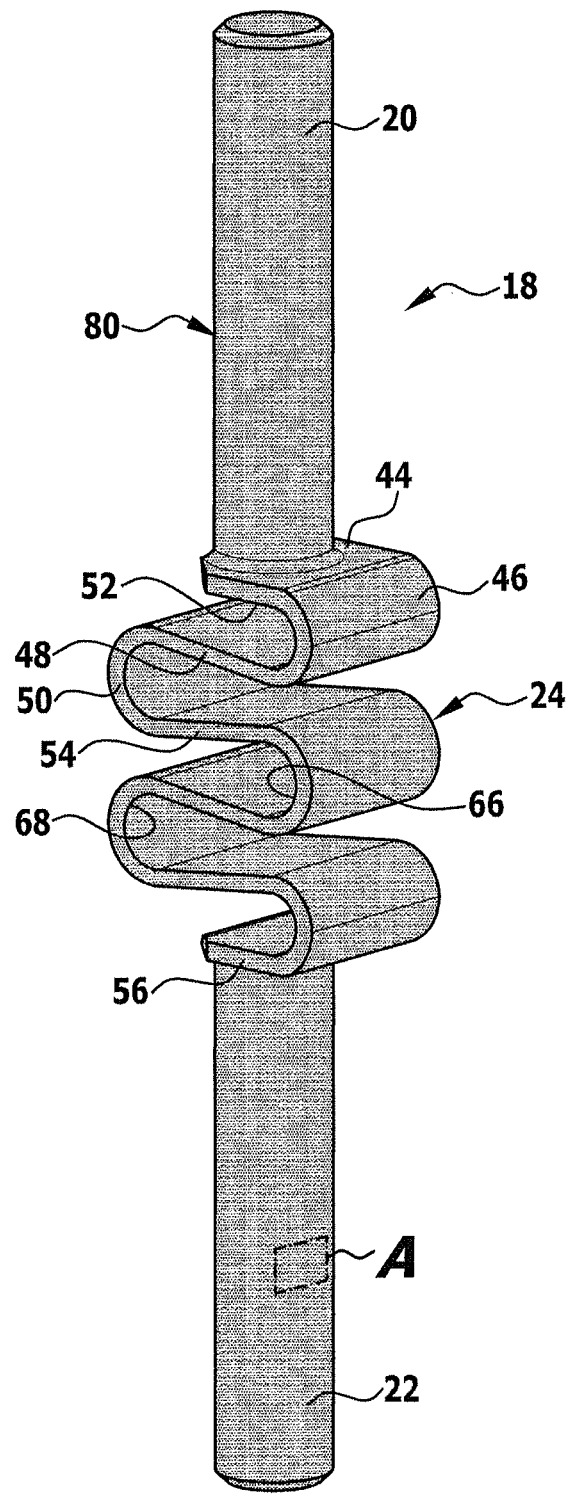
FIG. 10 shows a perspective view of a connecting element, the entire surface of which has been machined by a blasting process.

In FIG. 10 a connecting element 18 is shown diagrammatically, the outside surface 80 of which is completely blasted. For example, shot peening processes with balls 82 may be used as blasting process, the balls 82 being made of glass or steel. Shot peening is a cold working process in which the surface 80 of the connecting element 18 is blasted with balls 82, with each ball 82 that impacts the surface 80 acting like a tiny sledgehammer which leaves behind a shallow cup 84 on the surface. In order that a cup 84 can be produced, a surface layer of the connecting element 18 must be expanded. Deeper layers of material do, however, attempt to bring the surface 80 back into the original state. An area of cold-formed material with a high residual compressive stress is thereby produced in each case under the cups 84. Overlapping cups 84 produce a uniformly high residual compressive stress in an edge zone of the connecting element 18.

No cracks can arise and propagate within a residual compressive stress layer. Since almost all damage due to fatigue and stress cracking corrosion normally starts from the surface 80, a life span of the connecting element 18 is substantially increased by the shot peening. The residual compressive stresses produced by the shot peening in the surface layer amount to about half of the tensile strength of the material. With many materials, a surface hardness is also increased owing to the cold-work hardening by the shot peening.

As an alternative to the shot peening process, the so-called laser peening process may also be used. It is based on shock waves generated by pulsed laser radiation to produce residual compressive stresses. The residual compressive stress layer can be further enlarged, for example, by about a millimeter by the laser peening process.

Figure 11:
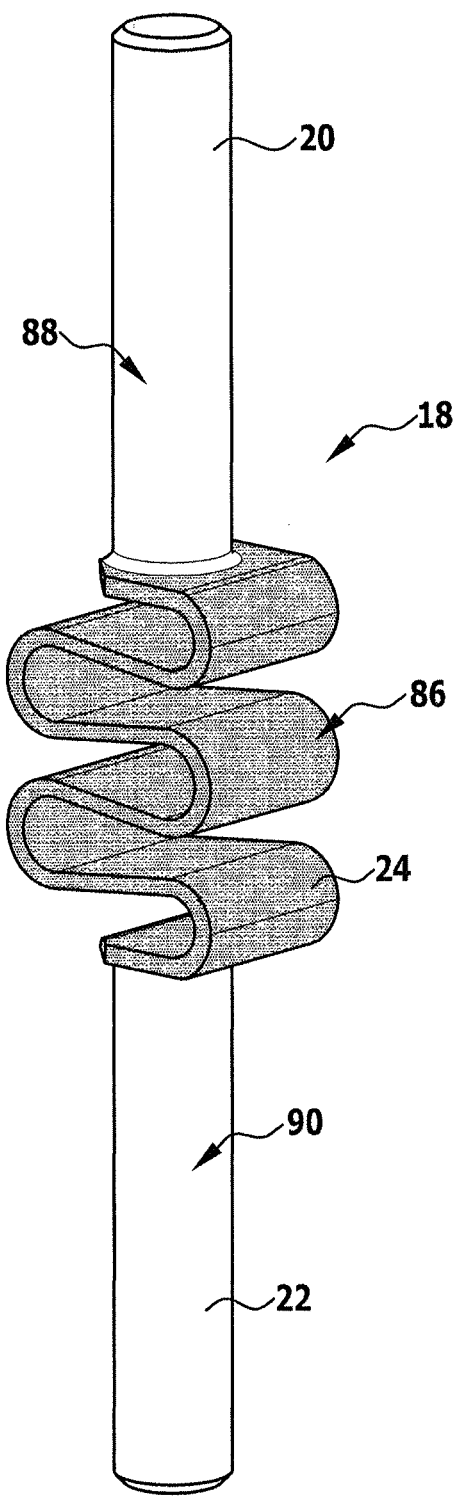
FIG. 11 shows a perspective view of a connecting element in which only the intermediate section has been machined by a blasting process.

As an alternative to the blasting treatment of the entire outside surface 80, it is possible, as in the connecting element 18 shown diagrammatically in FIG. 11, for only an outer surface 86 of the intermediate section 24 to be blast treated. Outer surfaces 88 and 90 of the attachment sections 20 and 22 are covered and, therefore, remain unblasted during the blast treatment of the intermediate section 24.

Figure 12:
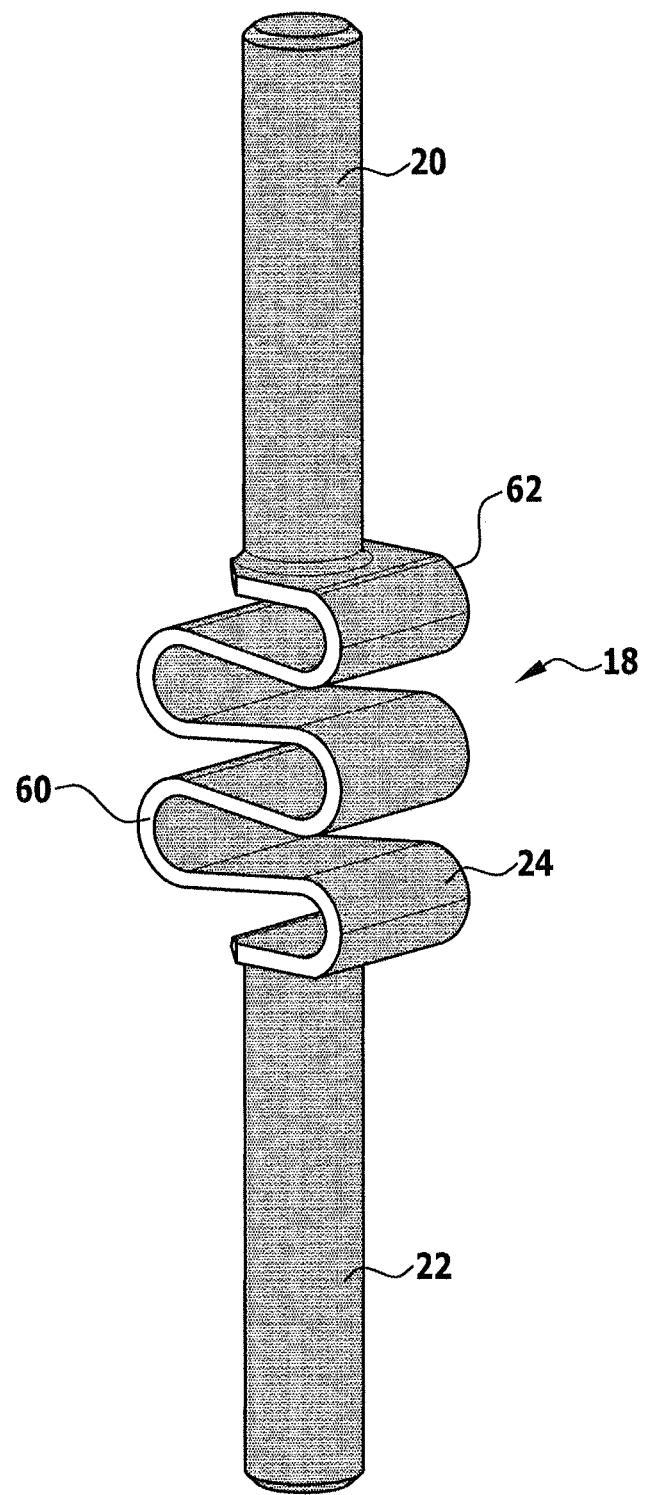
FIG. 12 shows a perspective view of a connecting element in which, with the exception of the side faces of the intermediate section, an outside surface has been completely machined by a blasting process.

The outside surface 80 defined by the outer surfaces 86, 88 and 90 may, as in the embodiment of a connecting element 18 shown diagrammatically in FIG. 12, also be completely blasted except for the side faces 60 and 62. These are covered during the blast treatment so that they remain unblasted. The thin-walled intermediate section 24 is thereby prevented from undergoing plastic deformation at the side faces 60, 62. In the worst case, deformations at the sides caused by the shot peening may even have a detrimental effect as regards the endurance strength brought about by the blasting. In accordance with a size of the balls 82, the resulting cups 84 may, in particular, lie in an order of magnitude of the thicknesses 76 and 78.

Figure 13:
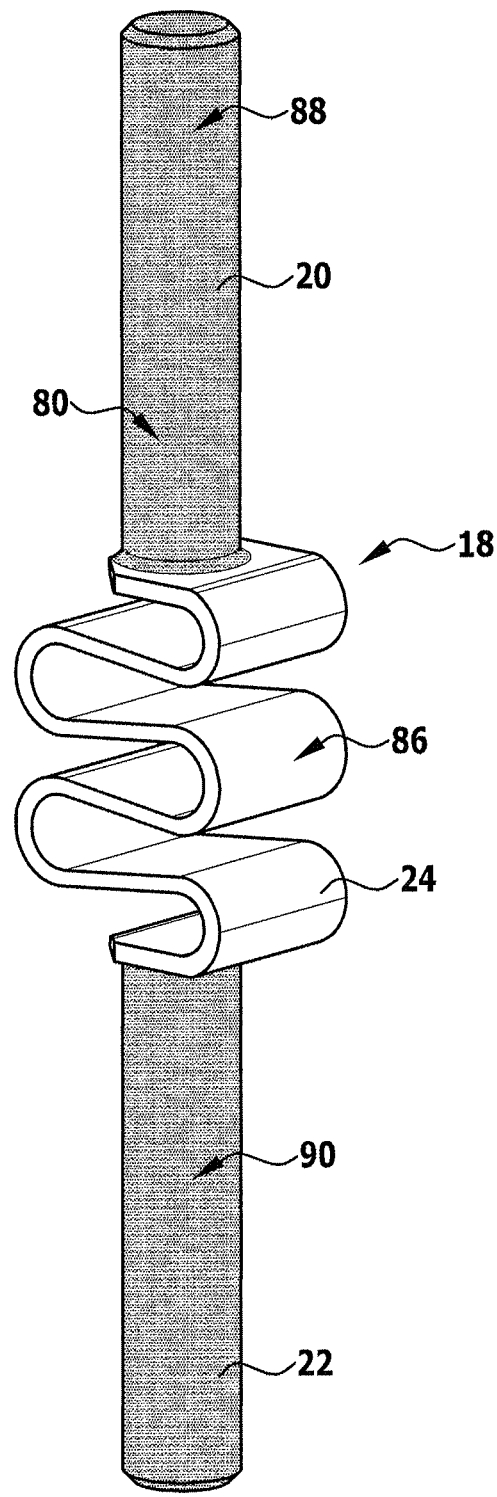
FIG. 13 shows a perspective view of a connecting element in which only surfaces of the attachment sections, but not of the intermediate section, have been machined by a blasting process.
Figure 14:
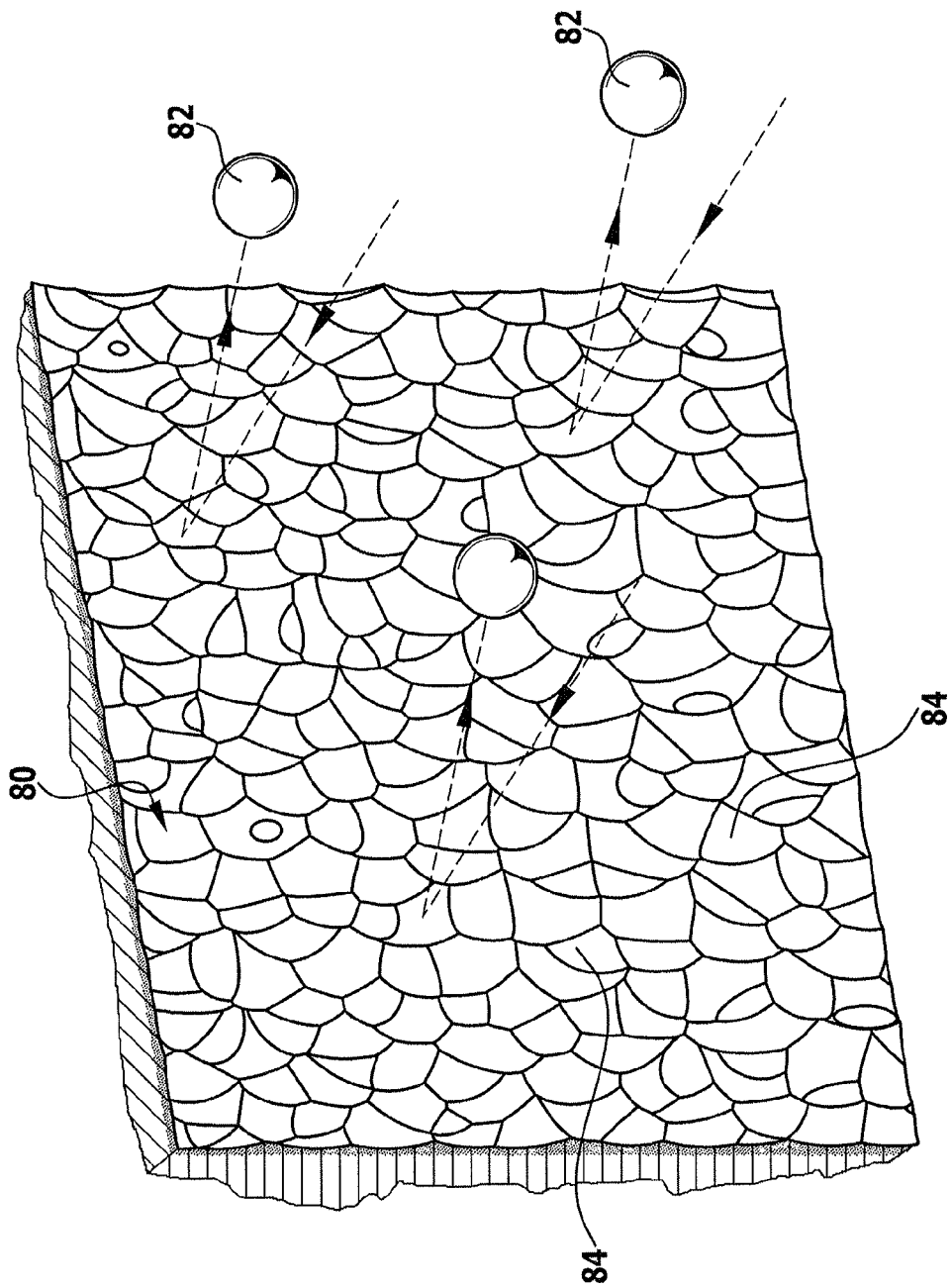
FIG. 14 shows an enlarged diagrammatic view of area A from FIG. 10.

A further variant of a partially blasted outside surface 80 of a connecting element 18 is shown diagrammatically in FIG. 13. Herein only the outer surfaces 88 and 90 are blast treated. The intermediate section 24 remains unblasted as it is completely covered during the blast treatment.

Figure 4:
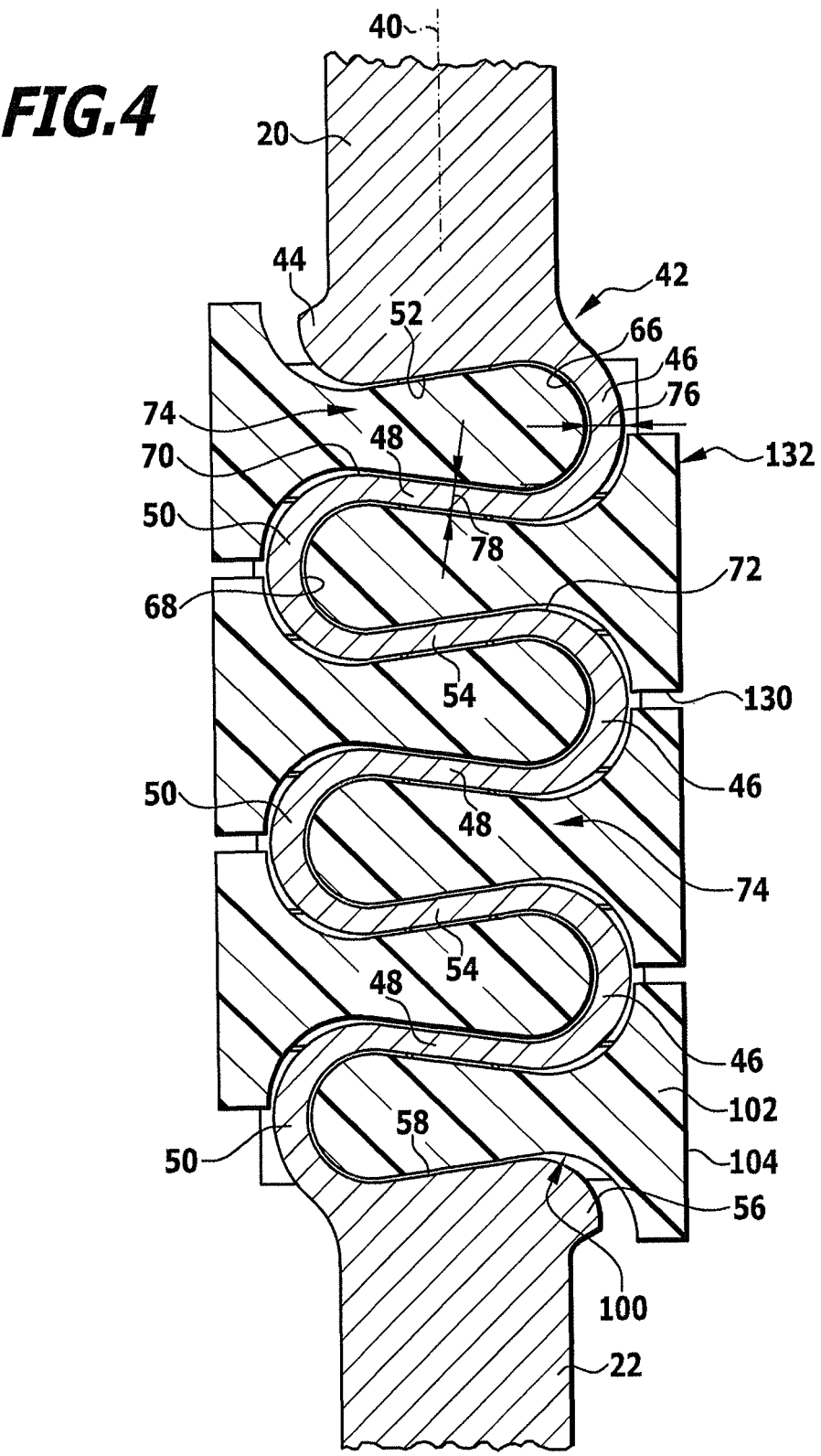
FIG. 4 shows a sectional view along line x-x in FIG. 2.

In order to influence the mechanical properties, in particular, a stiffness of the intermediate section 24 of the connecting element 18, movement limiting members 92 are provided in accordance with the number of recesses 66, 68 defined by the intermediate section 24. Each movement limiting member 92 comprises a filling body 94 which, in section, as shown diagrammatically in FIG. 4, is essentially drop-shaped and with play almost fills out the recesses 66, 68.

Each movement limiting member 92 further comprises a stop device 96 which acts parallel or substantially parallel to the longitudinal axis 40 and, in alternative embodiments also selectively, in the circumferential direction in relation to the longitudinal axis 40. The filling body 94, therefore, engages in a normal position of the connecting element 18, in which no external forces act on the intermediate section 24, for example, forces introduced via the attachment sections 20, 22, at least partially in a recess 66, 68. A width of the filling body 94 is somewhat larger than a spacing 98 between the side faces 60 and 62.

The filling body 94 also has a cross-sectional taper 100, which may also be referred to as constriction. As shown diagrammatically in FIG. 4, this is located in the area of the insertion opening 70 and 72, respectively, when the filling body 94 is inserted in a recess 66, 68.

Starting from the cross-sectional taper 100, the filling body 94 widens again and continues into a small substantially plate-shaped closing element 102, with which the insertion opening 70, 72 can be closed practically completely. An outer surface 104 of the closing element 102 facing away from the longitudinal axis 40 is convexly curved and forms a section of a cylinder surface. The cross-sectional taper 100 on the movement limiting member 92 and the insertion openings 70 and 72 of reduced cross section provided at the recesses 66, 68 prevent the filling bodies 94 inserted into the recesses 66 and 68 in a direction of insertion represented by arrows 106 in FIG. 2 from being able to be removed from these again or from being able to get lost unless the insertion openings 70, 72 are widened, for example, by expanding the recesses 66 and 68 by alternately pivoting longitudinal axes of the attachment sections 20 and 22 relative to each other. Alternatively, the insertion openings 70 and 72 can be widened by applying a tensile force to the attachment sections 20 and 22 in a direction away from each other.

Each movement limiting member 92 is symmetrical in relation to the plane of symmetry 64 and comprises in addition to the closing element 102 at least one, in the embodiments shown in the Figures, two, side closure elements 108 for closing the recesses 66, 68 at the sides. The closure elements 108 have plane stop surfaces 110, which face in the direction towards the longitudinal axis 40 and extend parallel to each other. Outer surfaces 112 of the closure elements 108 facing away from the longitudinal axis 40 are convexly curved and form part of a cylinder surface. In particular, they continue from the directly adjacent outer surface 104 of the closing element 102.

Each closure element 108 has two stop surfaces 114 and 116 facing away from each other, which define planes extending perpendicularly to the longitudinal axis 40. A small cuboidal projection 118 protrudes from the stop surface 116. Also provided on each closure element 108 is a recess 120, which extends somewhat in the direction towards the longitudinal axis 40 into the filling body 94 and faces in a direction opposite to the projection 118.

Figure 2:
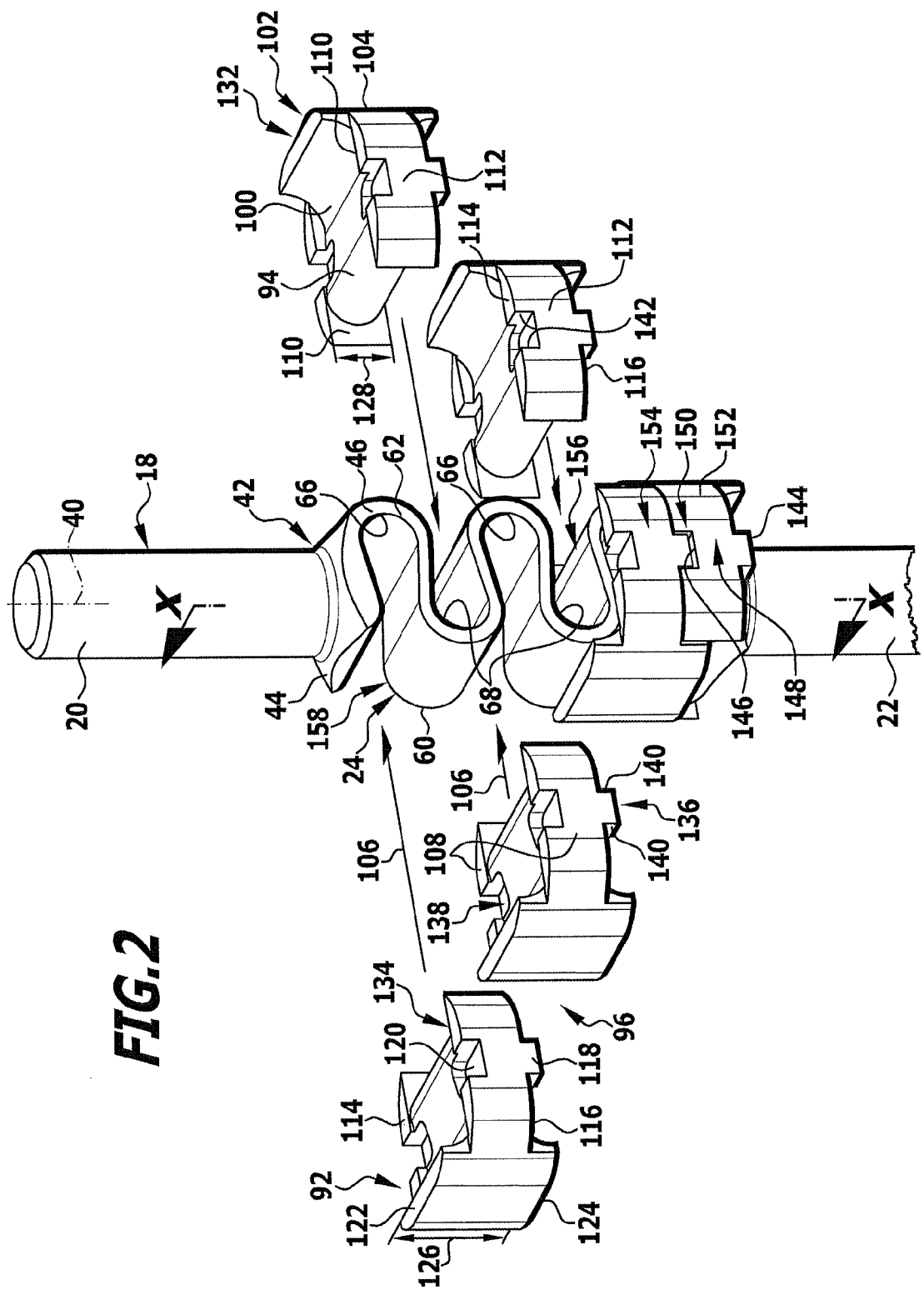
FIG. 2 shows a connecting element represented in FIG. 1 when assembling movement limiting members.
Figure 3:
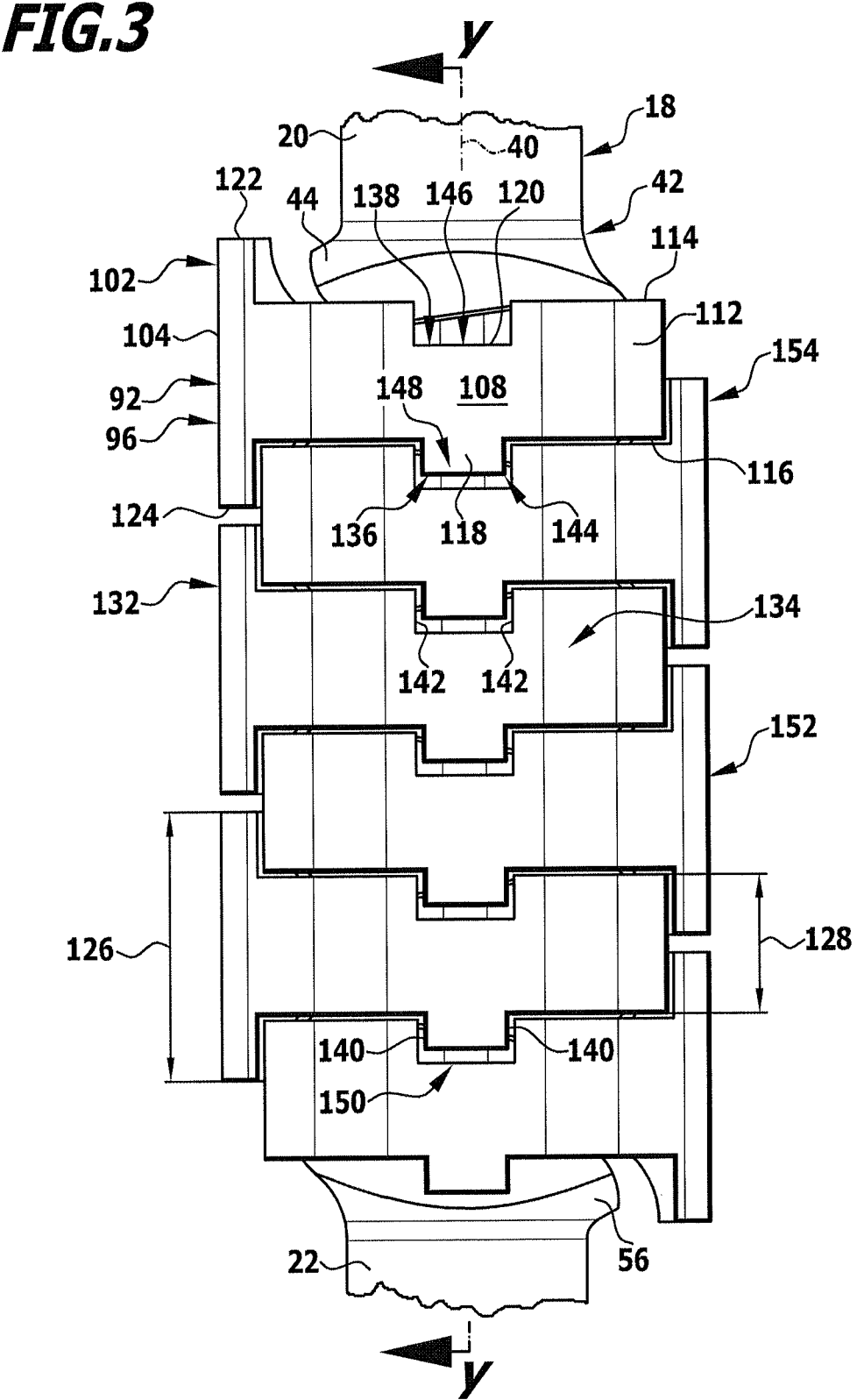
FIG. 3 shows an enlarged side view of an intermediate section of the connecting element from FIG. 1.

The movement limiting members 92 are alternately inserted with the filling bodies 94 into the recesses 66, 68, as shown diagrammatically in FIG. 2. The projections 118 and the recesses 120 are arranged and shaped such that a projection 118 engages substantially with positive locking in a recess 120 of a neighboring movement limiting member 92. In each case, a stop surface 114 of a movement limiting member 92 lies substantially with surface-to-surface contact against a stop surface 116 of the neighboring movement limiting member 92.

The closure elements 108 close the recesses 66, 68 on two opposite sides. Together with the closing element 102, this results in a substantially U-shaped arrangement of the closure elements 108 and the closing element 102, to close direct access to the recesses 66, 68 and engage around the intermediate section 24.

Figure 5:
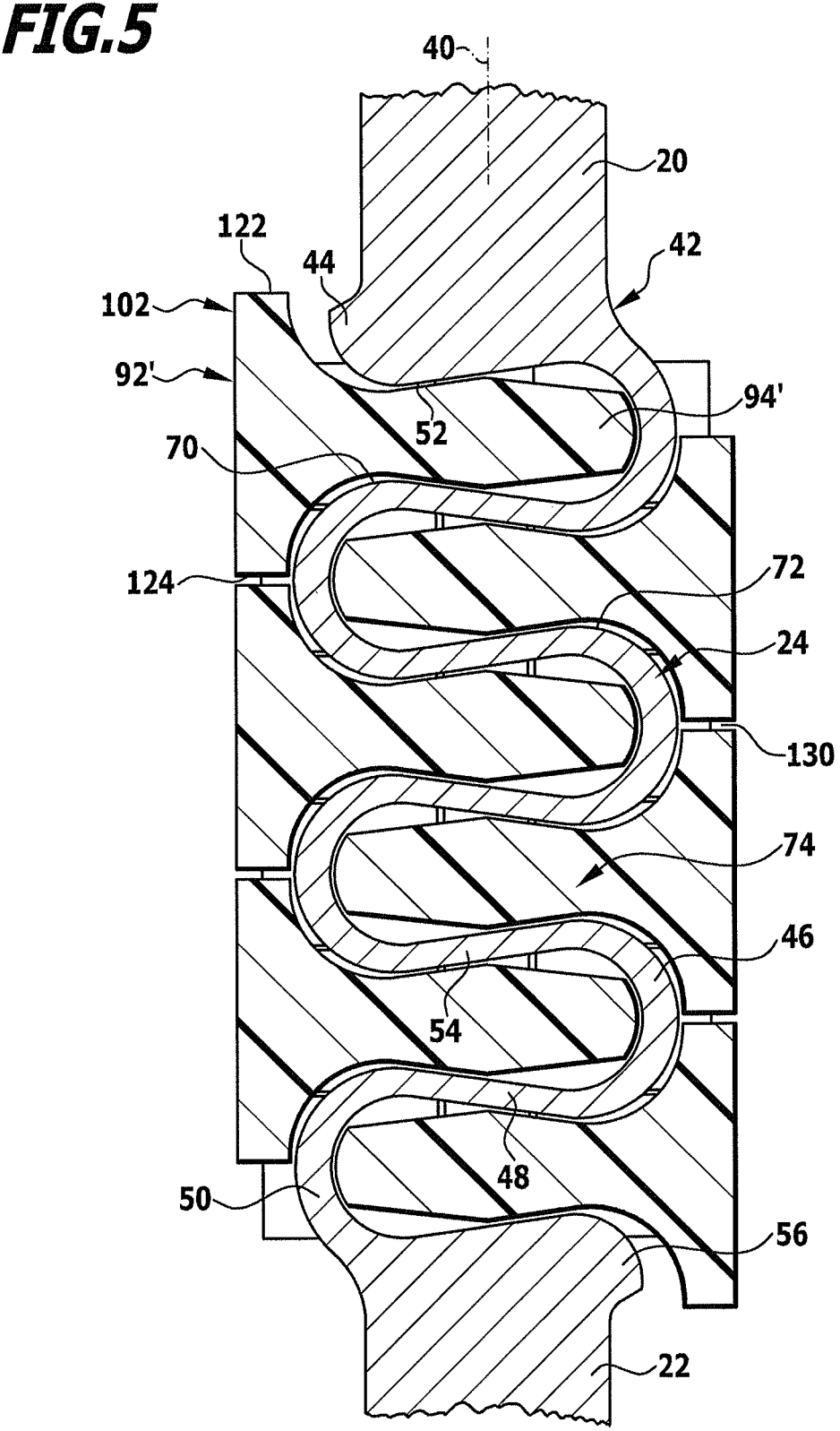
FIG. 5 shows a view in analogy with FIG. 4 with an alternative embodiment of movement limiting members.

Each closing element 102 has two stop surfaces 122 and 124 extending parallel to each other, which define planes extending perpendicularly to the longitudinal axis 40 and extend parallel to the stop surfaces 114 and 116. A spacing 126 between the stop surfaces 122 and 124 is only slightly smaller than twice a spacing 128 between the stop surfaces 114 and 116. Owing to the alternating arrangement of neighboring movement limiting members 92, as will be clear, in particular, from FIGS. 4, 5 and 7, stop surfaces 122 and 124 not of immediately neighboring movement limiting members 92, but of next but one movement limiting members 92 lie opposite each other. A gap 130 is defined between them in each case.

Figure 7:
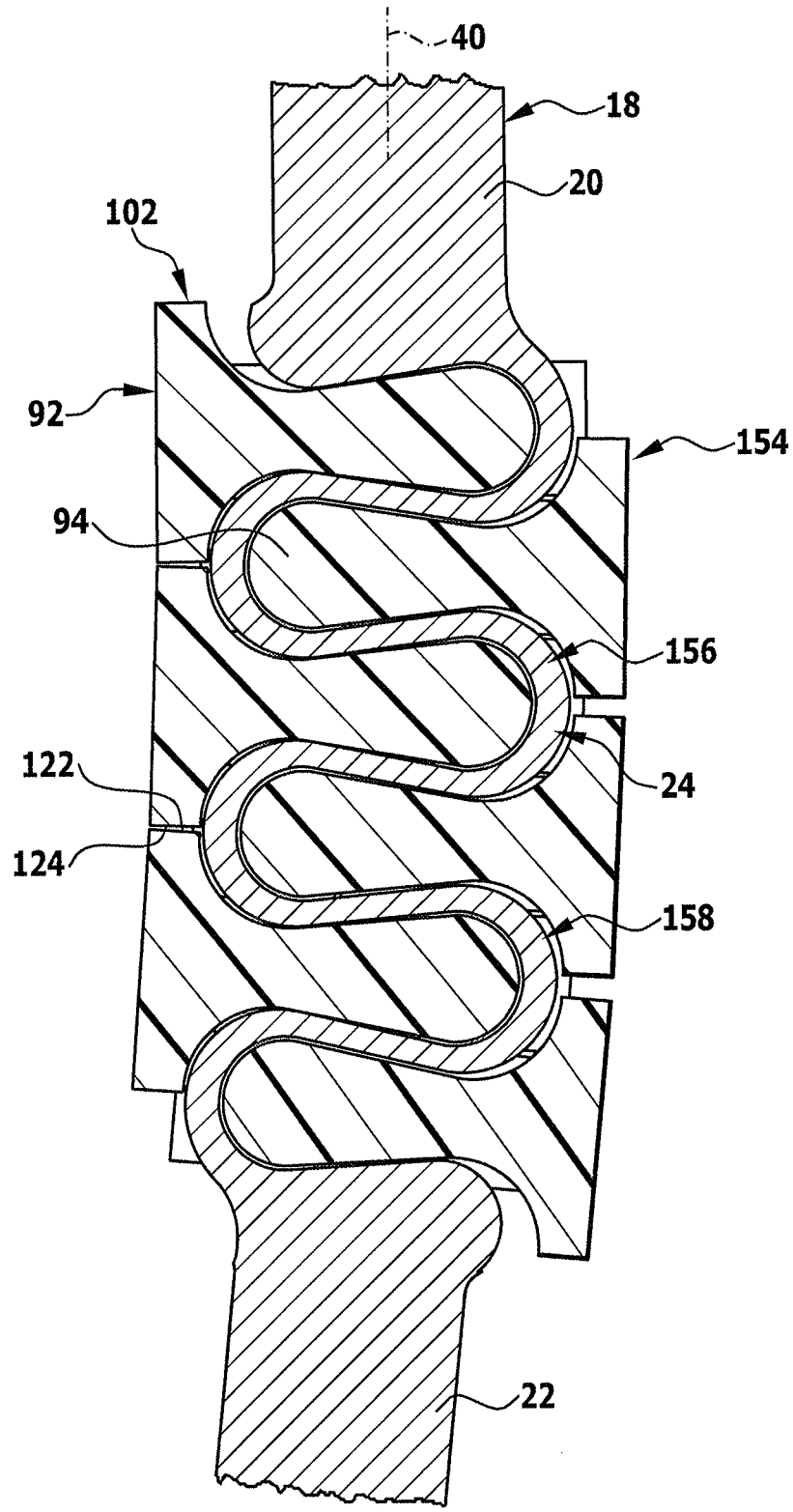
FIG. 7 shows a sectional view in analogy with FIG. 4 with bent intermediate section.

Both the closing element 102 and the closure elements 108 form stops 132 and 134, which serve to limit movement of the intermediate section 24. Bending of the intermediate section 24, as shown diagrammatically in FIG. 7, is only possible to such an extent until the stop surfaces 122 and 124 abut against each other. The stop surfaces 114 and 116 of the stops 134 limit, in particular, compression of the intermediate section 24.

The projections 118 form, as well as the recesses 120, further stops 136 and 138. Stop surfaces 140 of the stops 136 facing in the circumferential direction and stop surfaces 142 of the stops 138 facing in the circumferential direction interact in relation to the longitudinal axis 40 in the circumferential direction and prevent rotation of neighboring movement limiting members 92 about the longitudinal axis 40.

The projections 118 and the recesses 120 also form coupling members 144 and 146 of coupling devices, generally designated by reference numeral 148, which, in turn, themselves form part of an anti-twisting device, generally designated by reference numeral 150, which serves to substantially prevent twisting of the intermediate section 24 about the longitudinal axis 40. The anti-twisting device 150 thus comprises, in particular, the two stops 136 and 138 acting in the circumferential direction. Neighboring movement limiting members 92, whose filling bodies 94 engage in neighboring recesses 66, 68 of the intermediate section 24, can be coupled to each other by the coupling device 148. In the embodiments shown in the Figures, the coupling members 144 and 146 engage each other substantially with positive locking. All in all, each of the described movement limiting members 92 comprises two different coupling members 144 and 146, which are each allocated to a coupling device 148. The coupling members 144 and 146 are also formed so as to face in opposite directions and are aligned parallel or substantially parallel to the longitudinal axis 40.

Owing to the described configuration, the movement limiting members 92 in engagement with the intermediate section 24 define a common and substantially cylindrical enveloping contour 152.

The movement limiting members 92 are all of identical and one-piece construction. In particular, they are in the form of an injection molded part, more specifically, made of a biocompatible material. This is preferably a plastic, in particular, polyethylene, polyether ether ketone, polyurethane or polycarbonate urethane. Fiber-reinforcing plastics are also advantageous.

The connecting element 18 also comprises a resetting device 154 for automatically returning the connecting element 18 from a deflected position in which it is deflected from the normal position back into the normal position. The resetting device 154 comprises a resetting element 156 for automatically returning the connecting element 18 from the deflected position back into the normal position. It is, as in the embodiments shown in the Figures, in the form of a spring element 158. The spring element 158 is defined by a leaf spring wound in a serpentine manner, which forms the intermediate section 24.

Figure 6:
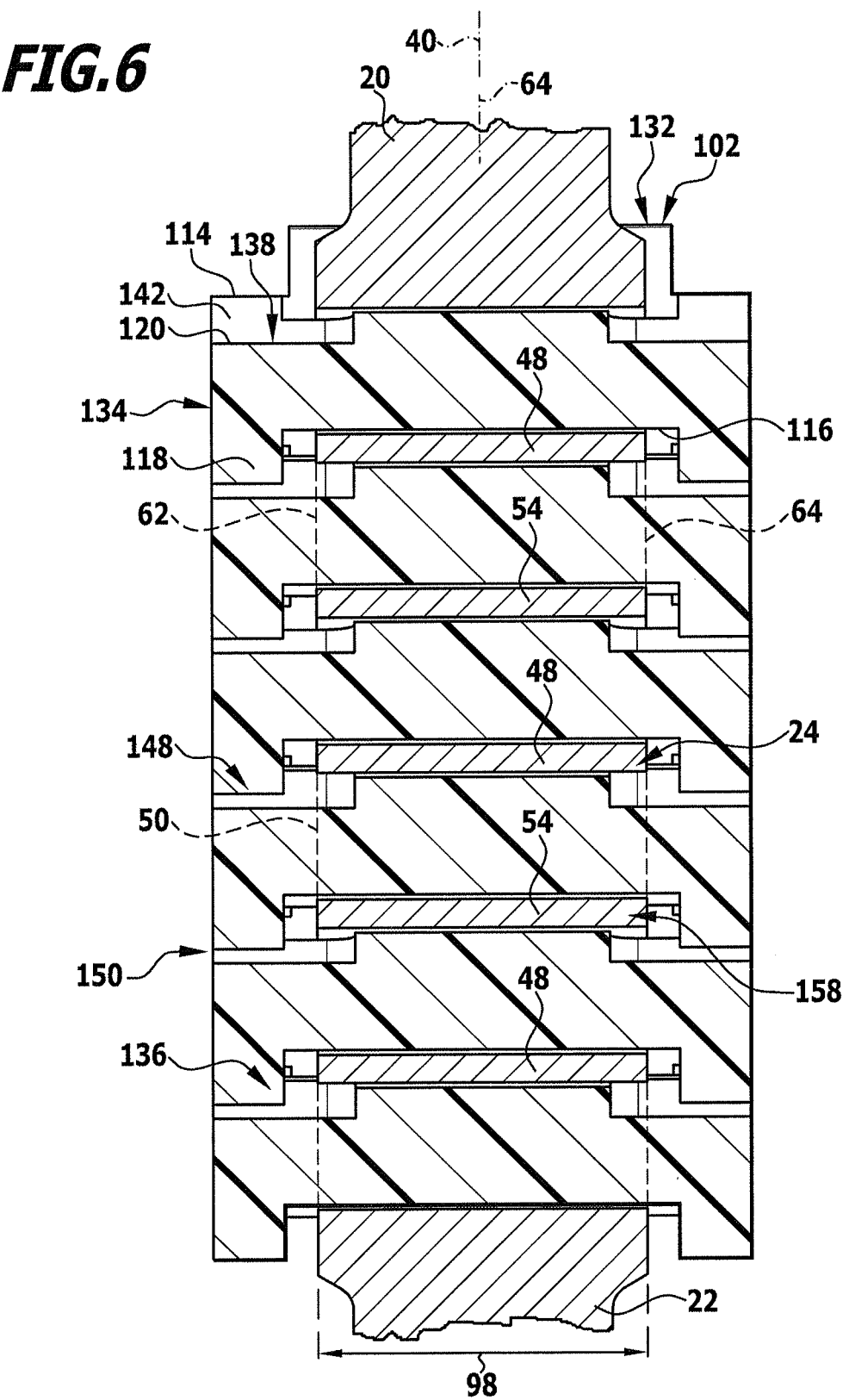
FIG. 6 shows a sectional view along line y-y in FIG. 3.

If the connecting element 18 is bent by pivoting the attachment sections 20 and 22 relative to each other, for example, in a sectional plane shown in FIGS. 4 and 7, then after releasing the attachment sections 20, 22, the connecting element is automatically transferred back again into the normal position shown in FIGS. 4 and 6, more specifically, by the resetting device 154.

Figure 8:
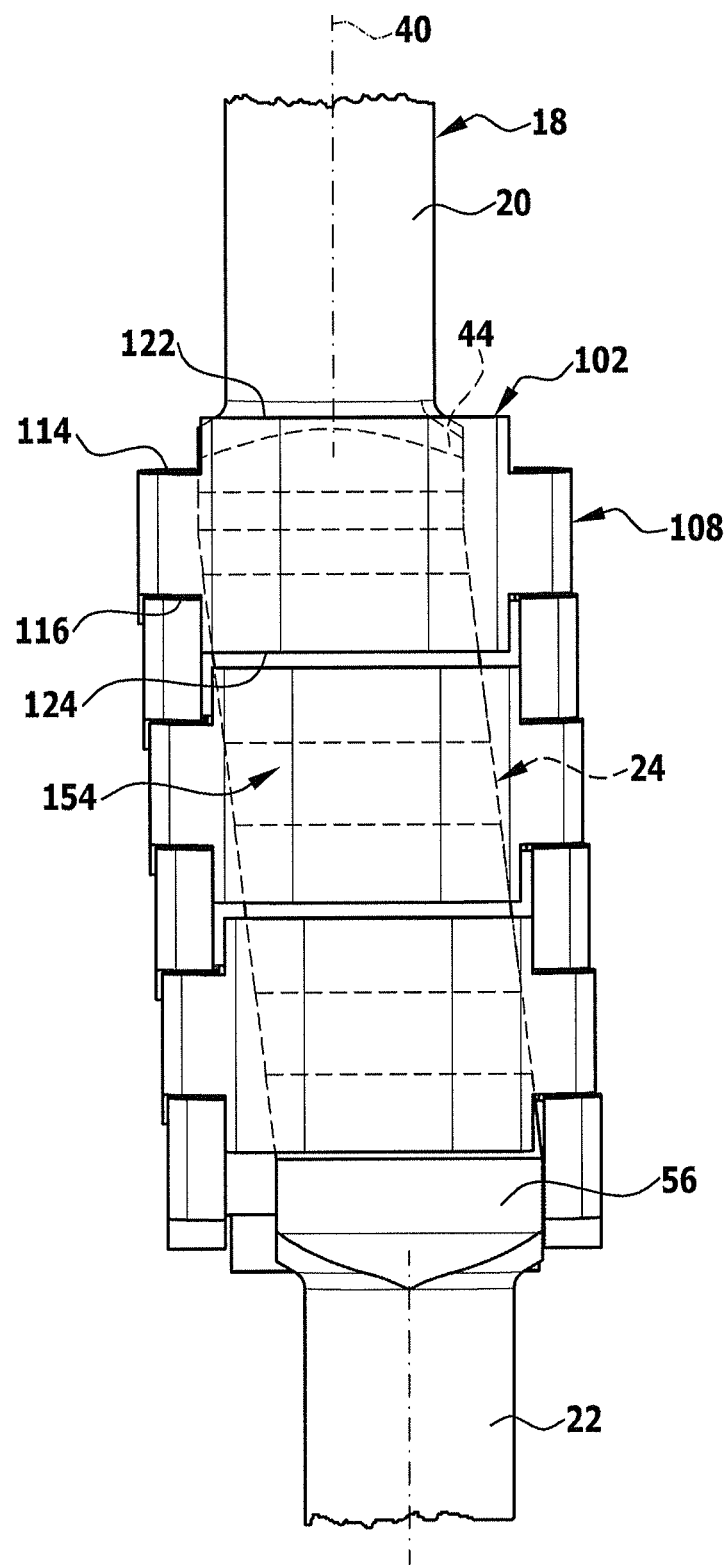
FIG. 8 shows a side view of a laterally pretensioned intermediate section.
Figure 9:
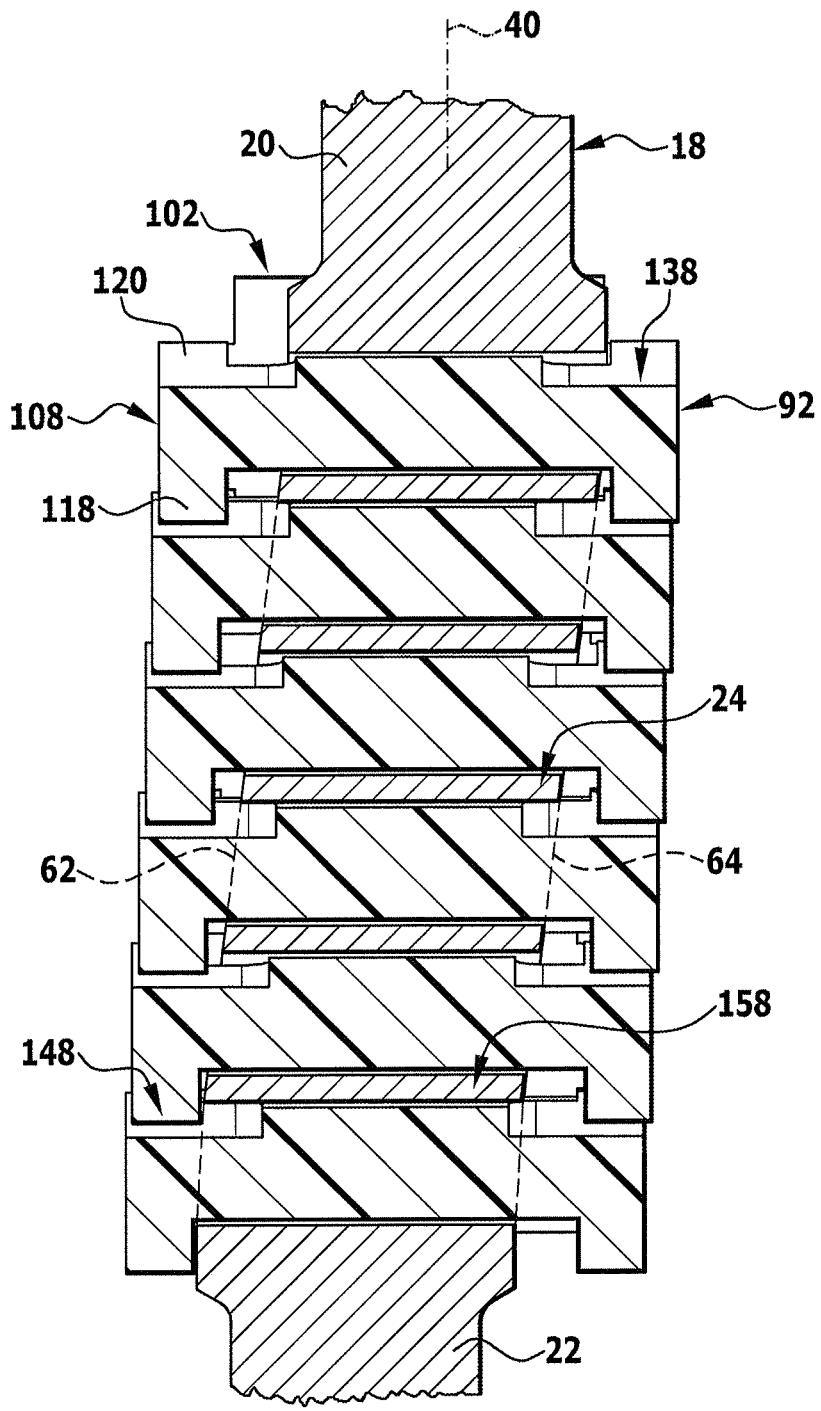
FIG. 9 shows a sectional view in analogy with FIG. 6 with lateral pretensioning as represented in FIG. 8.

A lateral pretensioning of the attachment sections 20, 22 relative to each other in a plane perpendicular to a flexion plane shown in FIGS. 4 and 6 results in a successive deflection of neighboring movement limiting members 92 in a direction perpendicular to the direction of insertion 106, as shown diagrammatically in FIGS. 8 and 9. A maximum deflection is, in turn, limited by the stops 136 and 138.

Stiffnesses of the connecting element 18 can be practically optionally set by selection of the materials from which the movement limiting members 92 are made and by selection of the materials from which the connecting element 18 is made. A maximum angle of flexion between the attachment sections 20, 22 can be defined by a height of the closing elements 102, i.e., by the spacing 126. At the same time, a width of the gap 130 is predefined by this spacing 126. The wider the gap, the greater is a possible flexion of the intermediate section 24.

The movement limiting members 92 can stabilize the stabilization system 10 for the vertebral column in the described manner. They serve, so to speak, as extension stoppers by limiting a movement of the intermediate section 24 under axial compression. Depending on play of the movement limiting members 92, a characteristic curve in compression can be influenced. This preferably leads to a progressive course of the characteristic curve.

Owing to the movement limiting members 92 embracing the intermediate section 24 from the outside and engaging one another mutually, they form, so to speak, an outer chain of members around the intermediate section 24. The effective forces are absorbed by the closure elements 108. A stiffness of the connecting element 18 under shear is therefore increased. At the same time, this means an increase in the stiffness of the connecting element 18 in axial rotation.

In addition, the coupling devices 148 serve to lock the movement limiting members undetachably to one another and to the intermediate section 24. As explained above, when assembling the movement limiting members 92, it is preferable to elastically bend open the intermediate section somewhat and, for example, starting from the attachment section 20, to insert the movement limiting members 92 one after the other into the recesses 66, 68.

In particular, assembly of the movement limiting members 92 can be simplified somewhat by a cross-sectional shape of the filling bodies 94 being changed. In the variant 92' of a movement limiting member shown diagrammatically in FIG. 5, an end of the filling body 94' facing away from the closing element 102 is of conically tapering configuration. Therefore, when assembling it, a widening of the insertion openings 70, 72 to a somewhat lesser extent is required in comparison with the movement limiting member 92.

What is claimed:

1. A connecting element for a stabilization system for the vertebral column, the connecting element comprising:
    a first attachment section for fixing to a first bone fixation device;
    a second attachment section for fixing to a second bone fixation device;
    an at least partially flexible intermediate section arranged or formed between the first and second attachment sections, said intermediate section having a serpentine shape defining at least one recess which is open at the sides in a direction transverse to a longitudinal axis defined by the intermediate section, the at least one recess delimited by two sections and defining an insertion opening, the two sections extending toward one another in the direction of the insertion opening to define a constriction at the insertion opening; and
    an anti-twisting device,
    wherein at least one movement limiting member is provided, which comprises a filling body and at least one stop device acting at least in one of a direction parallel or substantially parallel to the longitudinal axis and a circumferential direction, the filling body having a cross-sectional taper defining a constriction,
    wherein the filling body, in a normal position in which no external forces act on the intermediate section, engages at least partially in the at least one recess, with the constriction defined by the filling body engaging the constriction defined in the insertion opening to substantially prevent removal of the filling body from the at least one recess, and
    wherein the anti-twisting device prevents twisting of the intermediate section about the longitudinal axis.

2. A connecting element in accordance with claim 1, wherein the stop device comprises at least one stop which is at least one of arranged on, formed on and protruding from the filling body and acts at least in one of a direction parallel or substantially parallel to the longitudinal axis and a circumferential direction.

3. A connecting element in accordance with claim 1, wherein stop devices of neighboring movement limiting members, in the normal position, lie at least partially in a non-contacting manner opposite each other and, in a position deflected from the normal position, lie against each other.

4. A connecting element in accordance with claim 1, wherein each movement limiting member comprises a stop device with two stops facing in opposite directions.

5. A connecting element in accordance with claim 1, wherein at least one of the at least one movement limiting member and the intermediate section is formed mirror-symmetrically in relation to a mirror plane containing the longitudinal axis.

6. A connecting element in accordance with claim 1, wherein the anti-twisting device comprises at least one coupling device for coupling neighboring movement limiting members whose filling bodies engage in neighboring recesses of the intermediate section.

7. A connecting element in accordance with claim 6, wherein the at least one coupling device comprises first and second coupling members which are in engagement with at least one of force and positive locking, and wherein a first coupling member of a movement limiting member faces in the direction of the second coupling member of a movement limiting member which is at least partially in engagement with a neighboring recess.

8. A connecting element in accordance with claim 7, wherein the at least one first coupling member and the at least one second coupling member are aligned parallel to the longitudinal axis.

9. A connecting element in accordance with claim 1, wherein the insertion opening faces transversely to and away from the longitudinal axis for inserting the filling body in a direction transverse to and towards the longitudinal axis.

10. A connecting element in accordance with claim 9, wherein the movement limiting member comprises a closing element for closing the insertion opening.

11. A connecting element in accordance with claim 10, wherein closing elements of next but one movement limiting members, in the normal position, lie against each other or are spaced from each other by a gap.

12. A connecting element in accordance with claim 1, wherein the at least one recess is open at the sides facing in two directions opposite to each other, and wherein the at least one movement limiting member at least partially closes the at least one recess at least at one side.

13. A connecting element in accordance with claim 1, wherein the at least one movement limiting member comprises at least one side closure element for at least partially closing the at least one recess at the sides.

14. A connecting element in accordance with claim 1, wherein the at least one movement limiting member is made from a biocompatible material.

15. A connecting element in accordance with claim 1, wherein the at least one movement limiting member is of one-piece configuration.

16. A connecting element in accordance with claim 1, wherein the at least one movement limiting member is in the form of an injection molded part.

17. A connecting element in accordance with claim 1, wherein a plurality of movement limiting members in engagement with the intermediate section are provided, which define a common and substantially cylindrical enveloping contour.

18. A connecting element in accordance with claim 1, wherein the intermediate section is of elastic construction.

19. A connecting element in accordance with claim 1, wherein a stiffness of the intermediate section has a value ranging from about 30 N/mm to about 150 N/mm.

20. A connecting element for a stabilization system for the vertebral column, the connecting element comprising:
- a first attachment section for fixing to a first bone fixation device;
- a second attachment section for fixing to a second bone fixation device;
- an at least partially flexible intermediate section arranged or formed between the first and second attachment sections, said intermediate section having a serpentine shape defining at least one recess which is open at the sides in a direction transverse to a longitudinal axis defined by the intermediate section, the at least one recess delimited by two sections and defining an insertion opening, the two sections extending toward one another in the direction of the insertion opening to define a constriction at the insertion opening; and
- an anti-twisting device, said connecting element having an outside surface which is machined at least partially by a blasting process, wherein at least one movement limiting member is provided, which comprises a filling body and at least one stop device acting at least in one of a direction parallel or substantially parallel to the longitudinal axis and a circumferential direction, the filling body having a cross-sectional taper defining a constriction, wherein the filling body, in a normal position in which no external forces act on the intermediate section, engages at least partially in the at least one recess, with the constriction defined by the filling body engaging the constriction defined in the insertion opening to substantially prevent removal of the filling body from the at least one recess, and wherein the anti-twisting device prevents twisting of the intermediate section about the longitudinal axis.

21. A connecting element in accordance with claim 20, wherein the at least partially machined surface is machined by a shot peening process.

22. A stabilization system for the vertebral column, the stabilization system comprising:
- at least one first bone fixation device;
- at least one second bone fixation device; and
- a connecting element, said connecting element comprising:
  - a first attachment section for fixing to the at least one first bone fixation device;
  - a second attachment section for fixing to the at least one second bone fixation device;
  - an at least partially flexible intermediate section arranged or formed between the first and second attachment sections, said intermediate section having a serpentine shape defining at least one recess which is open at the sides transversely to a longitudinal axis defined by the intermediate section, the at least one recess delimited by two sections and defining an insertion opening, the two sections extending toward one another in the direction of the insertion opening to define a constriction at the insertion opening; and
  - an anti-twisting device, wherein at least one movement limiting member is provided, which comprises a filling body and at least one stop device acting at least in one of a direction parallel or substantially parallel to the longitudinal axis and a circumferential direction, the filling body having a cross-sectional taper defining a constriction, wherein the filling body, in a normal position in which no external forces act on the intermediate section, engages at least partially in the at least one recess, with the constriction defined by the filling body engaging the constriction defined in the insertion opening to substantially prevent removal of the filling body from the at least one recess, and wherein the anti-twisting device prevents twisting of the intermediate section about the longitudinal axis.

23. A stabilization system for the vertebral column in accordance with claim 22, wherein the stop device comprises at least one stop which is at least one of arranged on, formed on and protruding from the filling body and acts at least in one of a direction parallel or substantially parallel to the longitudinal axis and a circumferential direction.

\* \* \* \* \*